United States Patent
Dahlberg et al.

(10) Patent No.: US 9,839,432 B2
(45) Date of Patent: Dec. 12, 2017

(54) FEMORAL COMPRESSION SYSTEM

(75) Inventors: Mattias Dahlberg, Uppsala (SE); Tobias Adenmark, Uppsala (SE)

(73) Assignee: St. JUDE MEDICAL COORDINATION CENTER BVBA, Zaventem (BE)

( * ) Notice: Subject to any disclaimer, the term of this patent is extended or adjusted under 35 U.S.C. 154(b) by 152 days.

(21) Appl. No.: 13/702,224

(22) PCT Filed: May 31, 2011

(86) PCT No.: PCT/EP2011/058953
§ 371 (c)(1),
(2), (4) Date: Dec. 5, 2012

(87) PCT Pub. No.: WO2012/004056
PCT Pub. Date: Jan. 12, 2012

(65) Prior Publication Data
US 2013/0085524 A1    Apr. 4, 2013

Related U.S. Application Data

(60) Provisional application No. 61/352,175, filed on Jun. 7, 2010.

(30) Foreign Application Priority Data

Jun. 7, 2010    (SE) ..................................... 1050583

(51) Int. Cl.
*A61B 17/132*    (2006.01)
*A61B 17/135*    (2006.01)
*A61B 17/12*    (2006.01)

(52) U.S. Cl.
CPC .......... *A61B 17/132* (2013.01); *A61B 17/135* (2013.01); *A61B 17/1325* (2013.01); *A61B 17/1355* (2013.01); *A61B 2017/12004* (2013.01); A61B 17/132; A61B 5/02225; A61B 5/02208; A61B 5/022; A61B 5/0225; A61B 5/02233; A61B 5/4893; A61B 5/6848; A61B 5/706; A61B 17/12109; A61B 17/12136; A61B 2017/00199; A61B 2562/043; A61B 5/0002; A61B 5/0075; A61B 5/015; A61B 5/04886;

(58) Field of Classification Search
CPC .............. A61B 17/1325; A61B 17/135; A61B 17/1355; A61B 2017/12004;
(Continued)

(56) References Cited

U.S. PATENT DOCUMENTS 4,321,929 A * 3/1982 Lemelson et al. ............ 600/301
4,479,494 A * 10/1984 McEwen ........................ 606/202
(Continued)

FOREIGN PATENT DOCUMENTS

| EP | 0 462 088 A2 | 12/1991 |
|---|---|---|
| WO | WO 2007/016765 A1 | 2/2007 |
| WO | WO 2009/000665 A1 | 12/2008 |

*Primary Examiner* — Tuan V Nguyen
*Assistant Examiner* — Chima Igboko
(74) *Attorney, Agent, or Firm* — Foley & Lardner LLP

(57) ABSTRACT

The present invention relates to a femoral compression system (14) for applying compression against a puncture site of a vessel in a patient, and a method for applying compression with a femoral compression system. The compression system (14) comprises an inflatable compression element (15) adapted to apply a pressure against the puncture site, a tightening unit (23) adapted to extend around a part of, or the whole of, the patients body to fixate and to tighten the compression element (15) against the puncture site, a pump (16) adapted to inflate the compression element (15), a valve (17) adapted to deflate the compression element (15), a pressure transducer (18) adapted to sense the pressure within the compression element (15). The system further comprises a blood pressure pulse detector (19) adapted to sense the patient's blood pressure pulse and to generate a pulse signal in dependence thereto that is applied to a control unit (20) that is connected to the pump (16), valve (17) and pressure transducer (19), wherein the control unit (20) is adapted to control the pressure within the compression element (15) in dependence of the pulse signal, by applying control signals to said pump (16) and valve (17).

10 Claims, 4 Drawing Sheets

(58) Field of Classification Search
CPC ............... A61B 5/0492; A61H 9/0078; A61H 2230/30; A61H 2230/305; A61H 9/0092; A61H 2201/5071; A61H 1/006; A61H 2201/165; A61H 2201/5007; A61H 2201/5035; A61H 2201/5038; A61H 2201/5082; A61M 2025/1081; A61M 25/0017; A61M 25/0662; A61M 25/10; A61N 1/0502; A61N 1/0551; A61N 1/08; A61N 1/36017; A61N 1/36057; A61N 5/0613; A61N 5/10; C12N 15/113; C12N 2310/141; C12N 2320/30; C12N 2320/31; A61K 31/00; A61K 31/7088; A61K 45/06
USPC .......................................... 606/201, 202, 203
See application file for complete search history.

(56) References Cited

U.S. PATENT DOCUMENTS

| | | | |
|---|---|---|---|
| 4,501,280 A * | 2/1985 | Hood, Jr. ...................... | 600/490 |
| 5,307,811 A * | 5/1994 | Sigwart et al. ............... | 600/490 |
| 5,569,304 A | 10/1996 | Ulrich | |
| 6,299,629 B1 | 10/2001 | Gruenfeld et al. | |
| 7,166,123 B2 * | 1/2007 | Hovanes et al. ............... | 606/202 |
| 7,485,131 B2 * | 2/2009 | Hovanes et al. ............... | 606/202 |
| 8,758,390 B2 * | 6/2014 | McEwen et al. ............... | 606/203 |
| 2002/0016610 A1 | 2/2002 | Hovanes et al. | |
| 2004/0122469 A1 * | 6/2004 | Akerfeldt et al. ............. | 606/201 |
| 2004/0147956 A1 * | 7/2004 | Hovanes et al. ............... | 606/202 |
| 2004/0181157 A1 * | 9/2004 | Medero ............... | A61B 5/02225 |
| | | | 600/500 |
| 2005/0251070 A1 * | 11/2005 | Villani ......................... | 601/133 |
| 2006/0089667 A1 | 4/2006 | Ben-David | |
| 2007/0156013 A1 * | 7/2007 | Birk ............................... | 600/37 |
| 2008/0071202 A1 * | 3/2008 | Nardi et al. .................... | 601/98 |
| 2008/0139949 A1 * | 6/2008 | Caldarone ............ | A61H 9/0078 |
| | | | 600/490 |
| 2008/0177159 A1 | 7/2008 | Gavriely | |
| 2008/0262533 A1 * | 10/2008 | McEwen et al. ............... | 606/202 |
| 2008/0319328 A1 * | 12/2008 | Akerfeldt et al. ............. | 600/494 |
| 2009/0137884 A1 * | 5/2009 | Naghavi et al. ............... | 600/309 |
| 2011/0238107 A1 * | 9/2011 | Raheman ....................... | 606/202 |

* cited by examiner

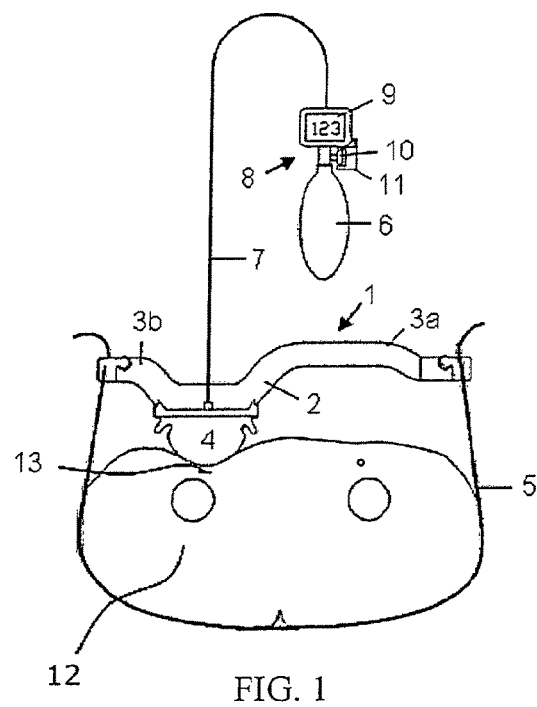
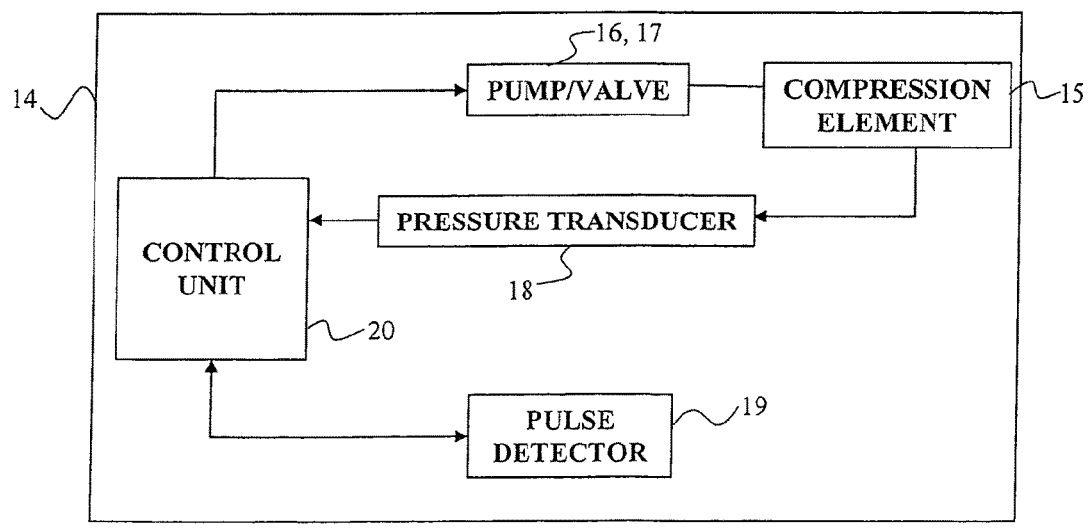
FIG. 1
FIG. 2

FEMORAL COMPRESSION SYSTEM

FIELD OF THE INVENTION

The present invention relates to a femoral compression system for compression of a vessel according to the preamble of the independent claims.

The present invention also relates to a method for applying compression of a vessel with the femoral compression system.

BACKGROUND OF THE INVENTION

To access a patient's vascular system for an invasive medical procedure such as catheterization or similar procedures, a puncture is made in e.g. the femoral artery. Following the medical procedure the flow of blood through the puncture site has to be stopped, so that haemostasis may begin as soon as possible. This may be done by using a compression device.

One example of such a compression device is known from WO 2009/000665, which is assigned to the same assignee as in the present application, describing a femoral compressing device for compressive bearing against the femoral artery of a patient. The device comprises a base plate, an inflatable air cushion, and a manometer connected to the inflatable air cushion. The device is fixed around the patient's body with a belt. In use, the inflatable air cushion is positioned over the femoral artery, and the belt is tightened and secured around the patient's body. To apply pressure to the femoral artery, the inflatable air cushion is inflated by a pump to a certain predetermined pressure, which is read from a pressure gauge.

When reducing the flow of blood passing a puncture site using a compression device a deficiency of blood supply to a part of the body, so called ischemia might occur. Thus, it would be desirable to be able to detect and register the patients pulse while stopping or reducing the blood flow passing the puncture site to lower the occurrency of ischemia.

Consequently, there is a need for an improved compression system for applying compression against a puncture site of a vessel in a patient, which minimizes the hospital resources needed and prevents unnecessary long procedures, and which system also helps to increase the patient integrity as the distance between the patient and health care professionals can be kept.

Further, there is a need for a system with a built-in control unit for controlling the pressure in the compression element when inflating or deflating.

SUMMARY OF THE INVENTION

The above-mentioned objects are achieved by the present invention according to the independent claim.

Preferred embodiments are set forth in the dependent claims.

Thus, according to the present invention a compression system comprising a pulse detector for automatically detecting the pulse is provided, which compression system regulates the pressure in the compression element, e.g. an inflatable air cushion, in dependence of the detected pulse.

The femoral compression system for applying compression against a puncture site of a vessel in a patient, in accordance with the present invention, comprises an inflatable compression element adapted to apply a pressure against the puncture site, a tightening unit adapted to extend around a part of, or the whole of, the patients body to fixate and to tighten the compression element against the puncture site, a pump adapted to inflate the compression element, a valve adapted to deflate the compression element, and a pressure transducer adapted to sense the pressure within the compression element. The system further comprises a blood pressure pulse detector adapted to sense the patient's blood pressure pulse and to generate a pulse signal in dependence thereto that is applied to a control unit that is connected to the pump, valve and pressure transducer, wherein the control unit is adapted to control the pressure within the compression element in dependence of the pulse signal, by applying control signals to the pump and valve.

Advantageously, the present invention in general, and in particular when applying a dedicated compression schedule, helps to optimize hemostasis, minimize the hospital resources needed, and prevent unnecessary long procedures, and increase the patient integrity.

SHORT DESCRIPTION OF THE APPENDED DRAWINGS

FIG. 1 shows an example of a femoral compression device, according to the prior art.

FIG. 2 shows a schematic block diagram illustrating the femoral compression system for applying compression against a puncture site of a vessel in a patient according to the present invention.

DETAILED DESCRIPTION OF PREFERRED EMBODIMENTS OF THE INVENTION

Figure 3:
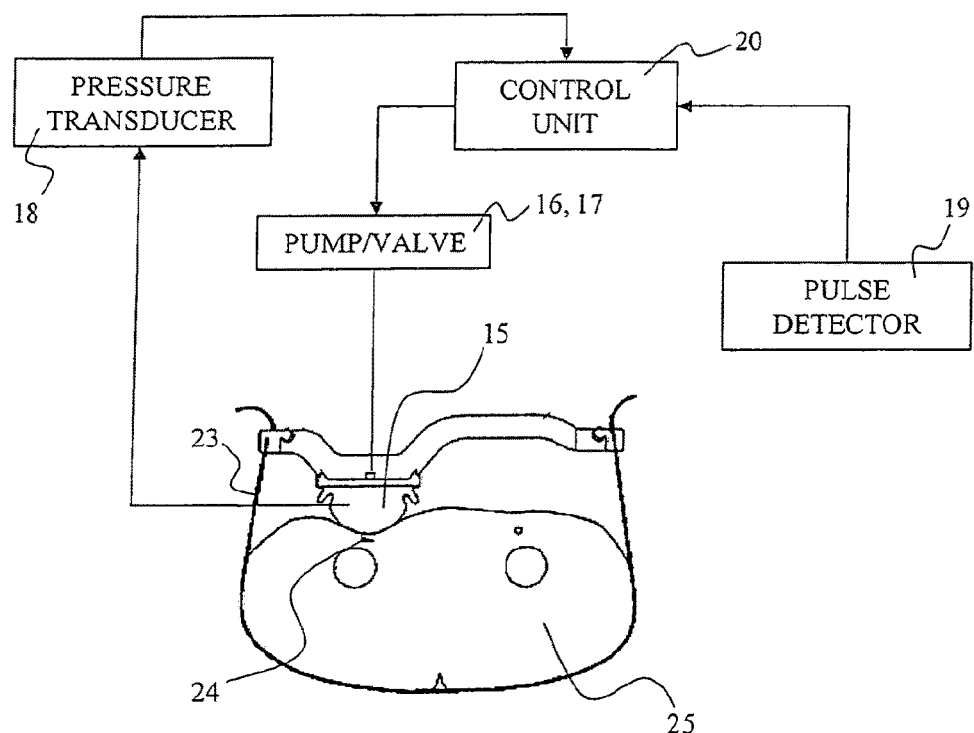
FIG. 3 shows the compression element 15, according to the present invention, when in use.

FIG. 1 illustrates a femoral compression device 1, according to the prior art, and as described in WO 2009/000665. The device 1 comprises a base plate 2 with two extensions 3a and 3b, a compression element 4, here in the shape of an inflatable and semi-spherical air cushion, a belt 5, a pump 6, an air connection 7, and an electric pressure gauge or manometer 8 with display 9. In use, compression element 4 is positioned over the femoral artery 13 of a patient 12, and the belt 5, which extends from the end of the first extension 3a, around the patient's body 12 and to the end of the second extension 3b, is tightened and secured by belt fasteners at the end of each extension. To apply pressure to the femoral artery 13, the inflatable semi-spherical air cushion 4 is inflated by the pump 6 to a certain pressure, which is measured by the manometer 8 and displayed on the display 9. The manometer 8 comprises further a vent knob 10, which is covered by a cap 11.

In FIG. 2, a femoral compression system 14 for applying compression against a puncture site of a vessel in a patient, according to the present invention, is disclosed. The femoral compression system 14, comprises an inflatable compression element 15 adapted to apply a pressure against the puncture site, a tightening unit (not shown in FIG. 2) adapted to extend around a part of, or the whole of, the patients body to fixate and to tighten the compression element 15 against the puncture site, a pump 16 adapted to inflate the compression element 15, a valve 17 adapted to deflate the compression element 15, and a pressure transducer 18 adapted to sense the pressure within the compression element 15.

As also illustrated in FIG. 2, the compression system 14 further comprises a blood pressure pulse detector 19 adapted to sense the patient's blood pressure pulse and to generate a pulse signal in dependence thereto that is applied to a control unit 20 that is connected to the pump 16, valve 17 and pressure transducer 18, wherein the control unit 20 is adapted to control the pressure within the compression element 15 in dependence of the pulse signal, by applying control signals to the pump and valve.

FIG. 3 shows the compression element 15, when in use. In a similar way as in the femoral compression device according to the prior art, shown in FIG. 1, the compression element 15, here in the shape of an inflatable and semi-spherical air cushion, is positioned over the femoral artery 24 of a patient 25, and the tightening unit 23 extends around the whole of the patient's body 25. The compression element 15 is connected to the pump 16, the valve 17, and the pressure transducer 18, and furthermore, a control unit 20 is connected to the pump 16, valve 17 and pressure transducer 18, and also to the pulse detector 19.

Preferably, the pump is an electric air pump. The pump 16 and the valve 17 may be arranged as a separate unit or may be integrated in the control unit 20. As an obvious constructive variation, the pump 16 and the valve 17 may be arranged as separate units, or may be arranged in the same unit.

Figure 4:
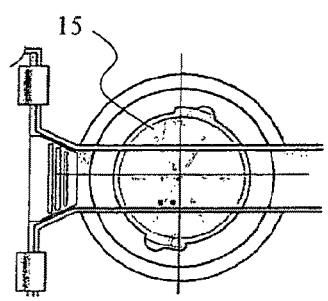
FIG. 4 shows the compression element 15, according to the present invention, seen from above.

FIG. 4 illustrates the compression element 15, in the shape of a semi-spherical air cushion, more in detail and seen from above, when positioned over a puncture site in the femoral artery of a patient's body.

According to the present invention, during startup of the compression system 14 the pulse detector 19 is activated to detect the patient's pulse. When the pulse is detected, the compression element 15 is inflated until the pulse is no longer detected by the pulse detector 19. Thereafter, the compression element 15 is deflated until the pulse detector 19 detects the pulse again. In this way the compression of the puncture site will be well-balanced, and the pressure exerted by the compression element 15 will be neither to high nor to low. If the compression is to low bleeding may possible occur, and if the compression is to high there is a risk of ischemia, as discussed above. However, during startup of the system 14, surveillance of the puncture site must be performed to identify possible bleeding.

The procedure may be fully or partly automated. According to one embodiment of the invention, the fully automated embodiment, the control unit 20 automatically controls the pump 16 and the valve 17. According to this embodiment, after the pulse has been detected, the compression element 15 has been inflated, and the pulse no longer is detected by the pulse detector 19, the control unit 20 is automatically, by means of the valve 17, adapted to release the pressure within the compression element 15 according to a predetermined "compression schedule". More specifically, the pressure transducer 18 senses the pressure within the compression element 15 and the control unit 20 is adapted to release the pressure according to a predetermined compression schedule stored in the control unit 20.

A compression schedule includes parameters required to control the system, i.e. with regard to max/min thresholds of the detected pulse; control parameters, i.e. response times, max/min inflated pressure. Many different compression schedules may be stored, where each schedule is set up e.g. with regard to different patient types. These parameters are entered into the control unit 20 and stored in the control unit 20, i.e in a compression schedule.

Figure 5:
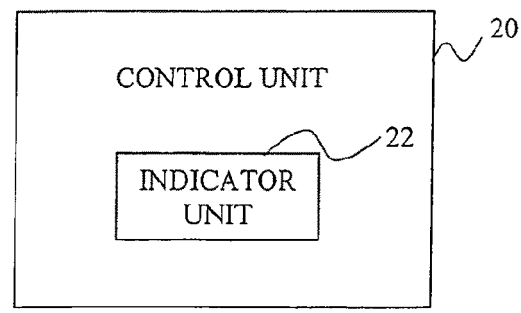
FIG. 5 shows a schematic view the control unit according to the present invention.

According to another embodiment of the present invention, the partly automated embodiment, the control unit 20 comprises an indicator unit 22 adapted to indicate to an operator when it is time to deflate the compression element 15, as also shown in FIG. 5. In this embodiment, after the pulse has been detected, the compression element 15 has been inflated, and the pulse no longer is registrated by the pulse detector 19, the indicator unit 22 indicates to the operator that it is time to deflate the compression element 15. The operator may then manually, by means of the valve 17, lower the pressure in the compression element 15. Thus, the control unit 20, or e.g. the pump 16 or the valve 17 may be provided with a display (not shown), which displays the actual pressure, sensed by the pressure transducer 18, within the compression element 15. The operator may then read the displayed pressure, and subsequently manually release an optional amount of the pressure, by means of the valve 17.

The control unit 20 may be provided with + and − buttons, which the operator may press in order to increase or decrease the pressure within the compression element 15. According to another embodiment, the control unit 20 may be provided with an "OK" button. When the operator presses the "OK" button, the control unit 20 sends a control signal to the valve 17 to lower the pressure to a predetermined subsequent pressure value.

Preferably, the control unit 20 is adapted to be able to be switched between the fully and partly automated states, in order to adapt the system 14 to the most suitable state in each specific case.

The pulse detector 19 is, according to the present invention, a pedal pulse detector, which is adapted to detect the pedal pulse. According to one embodiment of the present invention, the pulse detector 19 is arranged in relation to an inflatable cuff 21. In use, when the blood pressure is about to be measured, the inflatable cuff 21 is put around the patient's ankle and inflated, before startup of the system 14. Naturally, any other available pedal pulse detector type may be used, e.g. an optical, a piezoelectric or other type of electric pressure sensitive detector, or ultrasonic detector.

The control unit 20 of the system 14 is connected to the pulse detector 19, the pressure transducer 18 and the pump 16 and valve 17, via any standard signal interface, i.e. wireless, e.g. via Bluetooth, infrared signal, radio frequency signal, optical signal, or by wire.

The present invention also relates to a method for applying compression with a femoral compression system 14, against a puncture site of a vessel in a patient. The method includes:

a) providing an inflatable compression element 15 against said puncture site;

b) tightening said compression element 15 against said puncture site by means of a tightening unit 23 extending around a part, or the whole of the patients body;

c) detecting the patient's pulse by means of a pulse detector 19;

d) generating a pulse signal in dependence of the detected pulse, which pulse signal is applied to a control unit 20;

e) controlling the pressure within the compression element 15, by means of said control unit 20, in dependence of said pulse signal.

According to the method for applying compression with a femoral compression system 14 step e) may further include the steps of:

e1) inflating said compression element 15 by means of a pump 16 until the pulse no longer is detected by said pulse detector 19;
e2) deflating said compression element 15 by means of a valve 17 until the pulse is detected by said pulse detector 19 again.

As discussed above, said control unit 20 may, by applying control signals to said pump 16 and valve 17, control the pressure within the compression element 15 in accordance to one of many predetermined compression schedules.

Furthermore, and as also discussed above, said control unit 20 may indicate, by means of an indicator unit 22, that the pulse no longer is detected by said pulse detector 19, so that an operator manually may deflate said compression element 15, by means of said valve 17.

Figure 6:
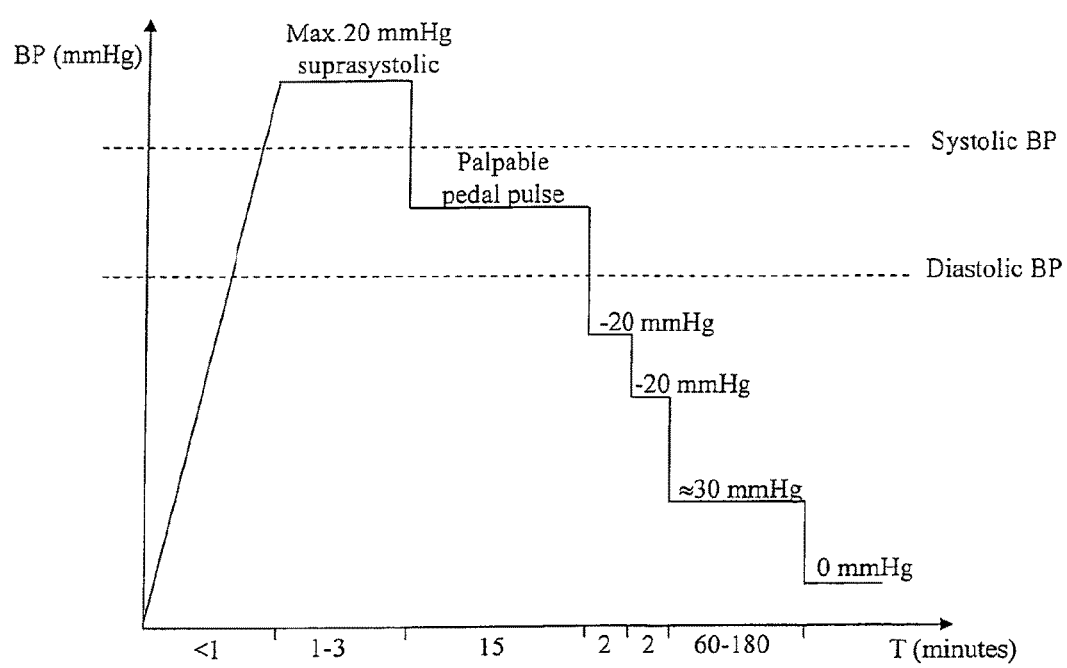
FIG. 6 shows a diagram, which schematically shows an example of a compression schedule according to the present invention.
Figure 7:
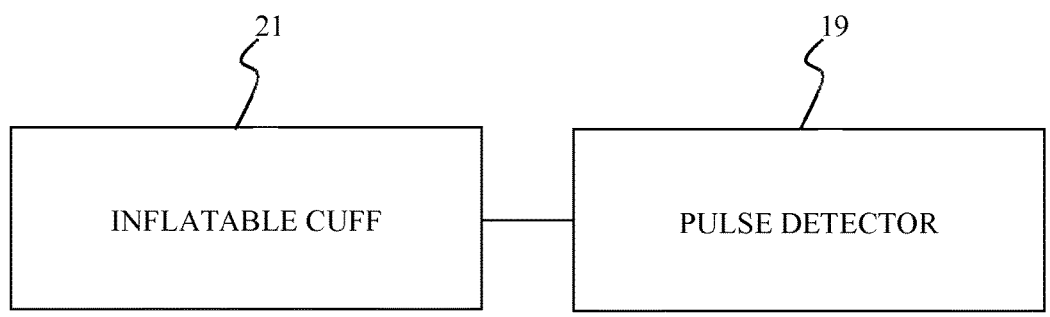
FIG. 7 is a block diagram schematically showing a pulse detector arranged in relation to an inflatable cuff.

An example of a compression schedule is shown in the diagram in FIG. 6. According to this compression schedule, after the compression element 15 has been applied, the pressure within the compression element 15 is, by means of the pump 16, increased until the pressure is 20 mmHg suprasystolic. At this pressure, no pedal pulse is detected. This pressure is kept for about 1-3 minutes, and thereafter the pressure is decreased until the pressure is approximately halfway between systolic and diastolic pressure. At this pressure it is checked that the pedal pulse is detected again. As shown in FIG. 6, the pressure is kept at this level for about 15 minutes. After that the pressure is decreased stepwise, e.g. first to a pressure approximately 20 mmHg below the diastolic pressure, and then yet another 20 mmHg, as also shown in FIG. 6. Finally, the pressure is kept at approximately 30 mmHg for about 60-180 minutes.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A femoral compression system for applying compression against a puncture site of a vessel in a patient, comprising:
   an inflatable compression element configured to apply a pressure against said puncture site;
   a belt configured to extend around a part of, or the whole of, the patient's body to fixate and to tighten the compression element against said puncture site;
   a pump configured to inflate said compression element;
   a valve configured to deflate said compression element;
   a pressure transducer configured to sense a pressure within said compression element and generate a pressure signal indicative of the pressure within said compression element;
   a blood pressure pulse detector configured to sense the patient's blood pressure pulse and to generate a pulse signal based on the patient's blood pressure pulse; and
   a control unit configured to: (i) receive the pressure signal from the pressure transducer, (ii) receive the pulse signal from the blood pressure pulse detector, (iii) control operation of the pump, and (iv) control operation of the valve,
   wherein, during operation of the compression system, the control unit controls the pressure within said compression element in accordance with a predetermined compression schedule, such that the control unit (i) controls the pump to inflate the compression element to a first elevated pressure at which the pulse signal indicates that no pulse is detected by the blood pressure pulse detector, (ii) maintains a pressure of the compression element at the first elevated pressure for a first duration, which is in a range of one to three minutes, (iii) after the first duration, controls the valve to deflate the compression element to a second elevated pressure at which the pulse signal indicates that a pulse is detected, (iv) maintains a pressure of the compression element at the second elevated pressure for a second duration that is longer than the first duration, and (v) after the second duration, controls the valve to further deflate the compression element.

2. The compression system according to claim 1, wherein said compression schedule comprises a maximum threshold of the detected pulse and a minimum threshold of the detected pulse.

3. The compression system according to claim 1, wherein said compression schedule is selected from a plurality of compression schedules that are stored in the control unit, each of the plurality of compression schedules being based on a different patient type.

4. The compression system according to claim 1, wherein said control unit is wirelessly connected to said pulse detector, said pressure transducer, said pump, and said valve.

5. The compression system according to claim 1, wherein said pulse detector is a pedal pulse detector.

6. The compression system according to claim 1, further comprising an inflatable cuff, wherein said pulse detector is arranged in relation to the inflatable cuff.

7. The compression system according to claim 1, wherein said control unit comprises an indicator unit adapted to indicate to an operator when it is time to deflate said compression element.

8. The compression system according to claim 1, wherein said compression schedule comprises a maximum inflated pressure and a minimum inflated pressure for the compression element.

9. The compression system according to claim 1, wherein, when the control unit controls the valve to further deflate the compression element, the control unit controls the valve to incrementally deflate the compression element.

10. The compression system according to claim 1, wherein the second duration is about 15 minutes.

* * * * *